United States Patent
Fujikawa et al.

(10) Patent No.: US 7,931,633 B2
(45) Date of Patent: Apr. 26, 2011

(54) BREAST MILK ABSORBENT PAD

(75) Inventors: Michiyo Fujikawa, Kagawa-Ken (JP);
Hikari Kawakami, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 964 days.

(21) Appl. No.: 11/759,956

(22) Filed: Jun. 8, 2007

(65) Prior Publication Data

US 2007/0287977 A1 Dec. 13, 2007

(30) Foreign Application Priority Data

Jun. 8, 2006 (JP) ................................. 2006-160341

(51) Int. Cl.
*A61F 13/15* (2006.01)
*A61F 13/20* (2006.01)

(52) U.S. Cl. .......... 604/385.07; 604/385.24; 604/385.27

(58) Field of Classification Search ............. 604/385.07, 604/385.24, 385.25, 385.27

See application file for complete search history.

(56) References Cited

U.S. PATENT DOCUMENTS

2005/0234411 A1* 10/2005 Ashton et al. ................. 604/358

FOREIGN PATENT DOCUMENTS

| JP | 2000-178805 | 6/2000 |
|----|-------------|--------|
| JP | 2001-011705 | 1/2001 |

OTHER PUBLICATIONS

English translation of specification of JP 2000-178805 A to Mikami et al.*

* cited by examiner

*Primary Examiner* — Melanie J Hand

(74) *Attorney, Agent, or Firm* — Brinks Hofer Gilson & Lione

(57) ABSTRACT

A breast milk absorbent pad according to the present invention comprises a pad chassis including a body fluid absorbent layer inclusive of a body fluid absorbent assembly and a body fluid leak-barrier sheet, and a pair of elastically stretchable and contractible members extending along transversely opposite sides of the pad-chassis in a longitudinal direction. The body fluid absorbent assembly is embossed so that the body fluid absorbent assembly may be formed along upper and lower ends thereof with high stiffness regions having a stiffness higher than that in the remaining region.

15 Claims, 5 Drawing Sheets

BREAST MILK ABSORBENT PAD

BACKGROUND OF THE INVENTION

The present invention relates generally to a breast milk absorbent pad adapted to be put on a wearer's skin so as to be covered with the other wearing article such as a brassiere.

Various types of a breast milk absorbent pad have conventionally been proposed and an example thereof preliminarily comprises a body fluid absorbent assembly, a liquid-barrier material facing away from a wearer's skin and an inner surface material facing the wearer's skin wherein the pad is provided along transversely opposite edges thereof with elastically stretchable and contractible members serving to deform the pad in a dome shape. Such dome shape permits the pad to be put on the wearer's breast with a good fit to avoid troubles such that the pad might slip down and breast milk might leak beyond a peripheral edge of the pad.

Such type of breast milk absorbent pad is well known, for example, from disclosures of Japanese Unexamined Patent application Publication No. 2000-178805 (hereinafter referred to as "Reference 1") and Japanese Unexamined Patent Application Publication No. 2001-11705 (hereinafter referred to as "Reference 2"). The breast milk absorbent pad disclosed therein generally comprises a pad-chassis composed of a liquid absorbent assembly and a liquid-barrier material fixed to the outer side of the absorbent assembly, and elastically stretchable and contractible members provided along transversely opposite edges of the pad-chassis so that a contractile force of these elastically stretchable and contractible members may deform the pad as a whole in a dome shape.

Usually, the breast milk absorbent pad may be inserted between the wearer's skin and the associated brassiere which has been spaced apart from the wearer's skin in order to wear the pad and the breast milk absorbent pad may be slipped down but not taken off in order to breast-feed a baby. In these cases, the type of breast milk absorbent pad as disclosed in References 1 and 2 may have the upper end of the pad unintentionally folded inward under the contractile force of the elastically stretchable and contractible members provided along the transversely opposite edges thereof. If it is intended to insert the breast milk absorbent pad having the upper end or the lower end folded inward between the brassiere and the wearer's skin from above or beneath, the folded upper or lower end may catch on the wearer's skin or the inner side of the brassiere and further folded inward or outward. Thus the breast milk absorbent pad as a whole may sometimes be folded inward or outward and it may be impossible to wear the breast milk absorbent pad. If it is intended to wear the breast milk absorbent pad folded in this manner, not only the pad will create a feeling of discomfort against the wearer's skin but also an effective area for absorption will be unacceptably reduced due to the liquid-barrier material folded inward or outward with respect to the pad, possibly resulting in leak of breast milk.

In addition, if the breast milk absorbent pad fastened to the brassier at a center thereof is slipped down in order to breast-feed her baby, the upper and lower ends of the breast milk absorbent pad already in a folded state will be further folded inward with respect to the breast milk absorbent pad under the contractile force of the elastically stretchable and contractible members. When the brassiere is repositioned after her baby has been breast-fed, the wearer must properly unfold the pad.

SUMMARY OF THE INVENTION

In view of the problem as has been described above, it is an object of the present invention to provide a breast milk absorbent pad improved so that the pad can be smoothly put on and taken off while the pad is retained in its shape curved in conformity to a shape of breast without any anxiety that upper and lower ends of the pad might be unintentionally folded inward.

The object set forth above is achieved, according to the present invention, by an improvement in the breast milk absorbent pad having a longitudinal direction and a transverse direction and comprising a pad-chassis having a first surface facing a wearer's skin and a second surface facing away from the wearer's skin, the pad-chassis being composed of a body fluid absorbent layer inclusive of a body fluid absorbent assembly and a body fluid leak-barrier sheet defining the second surface, and a pair of elastically stretchable and contractible members extending along transversely opposite sides of the pad-chassis in a longitudinal direction in order to deform the first surface in a concave shape.

The improvement according to the present invention is in that the body fluid absorbent assembly is provided along at least one of upper and lower ends thereof as viewed in the longitudinal direction with a high stiffness region having stiffness higher than in the region other than the high stiffness region.

The present invention includes preferred embodiments as will be described below.

At least an outer end of the high stiffness region as viewed in the longitudinal direction extends outward in the longitudinal direction beyond an associated end of the elastically stretchable and contractible member as viewed in the longitudinal direction.

The body fluid absorbent layer comprises the body fluid absorbent assembly composed of a body fluid absorbent core wrapped with a body fluid-spreadable sheet and a body fluid previous inner sheet facing the wearer's skin so as to cover the first surface of said body fluid absorbent assembly and the body fluid leak-barrier sheet comprises a body fluid impervious sheet.

The high stiffness region is formed by embossing.

The embossed high stiffness region is defined by a plurality of emboss lines spaced one from another by a given dimension in the transverse direction and extending in the longitudinal direction.

The embossed high stiffness region is defined by at least one emboss line continuously extending in the transverse direction.

The high stiffness region is provided on each of the upper and lower ends of the body fluid absorbent assembly.

The high stiffness region has a thickness smaller than in the remaining region except the high stiffness region.

The high stiffness region is formed by fixing a separately provided reinforcing layer to the body fluid absorbent assembly.

The pad-chassis has side flaps extending outward from transversely opposite edges of the body fluid absorbent assembly in the transverse direction, the elastically stretchable and contractible member comprising first and second pairs of elastically stretchable and contractible members spaced from each other in the transverse direction, the elastically stretchable and contractible members constituting the first pair are attached to the side flaps along the respective outer edges thereof while the elastically stretchable and contractible members constituting the second pair are attached to the side flaps along the respective outer edges of the body fluid absorbent assembly.

The side flaps comprise first portions defined by the inner sheet and second portions placed upon the first portions and defined by the leak-barrier sheet wherein the first pair of elastically stretchable and contractible members are attached to the second portions along the outer edges thereof while the second pair of elastically stretchable and contractible members are attached to the second portions along the inner edges thereof.

Elastically stretchable and contractible members are fixed within sleeves respectively formed by folding back transversely opposite edges of the leak-barrier sheet.

The inner sheet comprises a body fluid previous fibrous non-woven fabric and at least the transversely opposite edges of the leak-barrier sheet comprise a hydrophobic fibrous non-woven fabric.

The pad-chassis has end flaps extending outward from upper and lower ends of the body fluid absorbent assembly in the longitudinal direction.

The pad-chassis has a substantially elliptical outer shape.

In the breast milk absorbent pad according to the present invention, at least one of the upper and lower ends of the body liquid-absorbent layer includes the high stiffness region. Therefore it is unlikely that the lower end or the upper end might be caught by the wearer's skin and be unintentionally folded outward or inward as the breast milk absorbent pad is inserted between the brassiere and the wearer's skin to wear the pad. Consequentially, the pad can be smoothly inserted inside the brassiere without any feeling of discomfort which otherwise would be experienced by the wearer due to the folded upper and/or lower ends. Furthermore, there is no anxiety that the effective area of the body liquid-absorbent layer might reduced due to the body fluid leak-barrier sheet folded inward or outward. This is true also in the course of wearing the breast mild absorbent pad. Specifically, the peripheral edge of the breast milk absorbent pad can be stably put in close contact with the wearer's skin and thereby leak of breast milk can be effectively avoided.

The preferred embodiments of the present invention provide significant effects as will be described below.

In the embodiment of the invention wherein at least an outer end of the high stiffness region as viewed in the longitudinal direction extends outward in the longitudinal direction beyond the associated end of the elastically stretchable and contractible member as viewed in the longitudinal direction, at least the outer end portion of the high stiffness region is not affected by the contractile force of the elastically stretchable and contractible members and it can be reliably avoided that the pad-chassis might be folded.

In the embodiment of the invention wherein the high stiffness region is formed by embossing, the upper end and/or the lower end can be configured to be thinner than the remaining region and correspondingly the breast milk absorbent pad can be easily inserted between the brassiere and the wearer's skin from above or below.

In the embodiment of the invention wherein the side flaps comprise first portions defined by the inner sheet and second portions placed upon the first portions and defined by the leak-barrier sheet, the second portions of the body fluid leak-barrier sheet under the effect of the elastically stretchable and contractible members do not come in contact with the wearer's skin while the first portions of the inner sheet destined to come in direct contact with the wearer's skin are free from a direct effect due to the tensile stress of the elastically stretchable and contractible members. Consequentially none of gathers are formed on the first portions of the inner sheet, which would leave compression marks on the wearer's skin and sometimes make the wearer experience a feeling of discomfort. In this way, the first portions of the inner sheet are reliably kept in close contact with the wearer's skin and thereby effectively prevent leak of breast milk.

DETAILED DESCRIPTION OF THE PREFERRED EMBODIMENTS

Details of a breast milk absorbent pad according to the present invention will be more fully understood from the description given hereunder with reference to the accompanying drawings.

Figure 1:
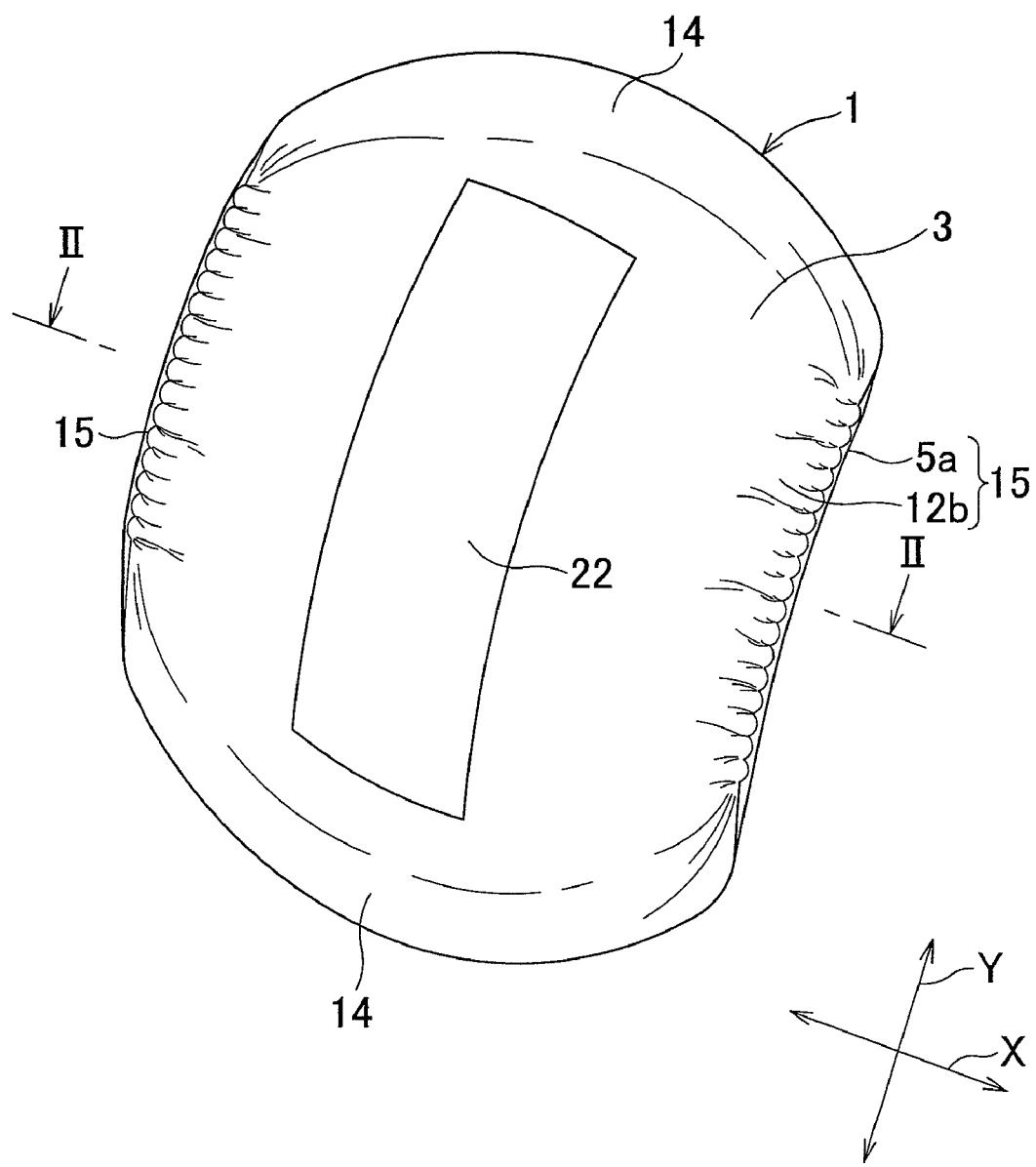
FIG. 1 is a perspective view of a breast milk absorbent pad as viewed from outside.
Figure 2:
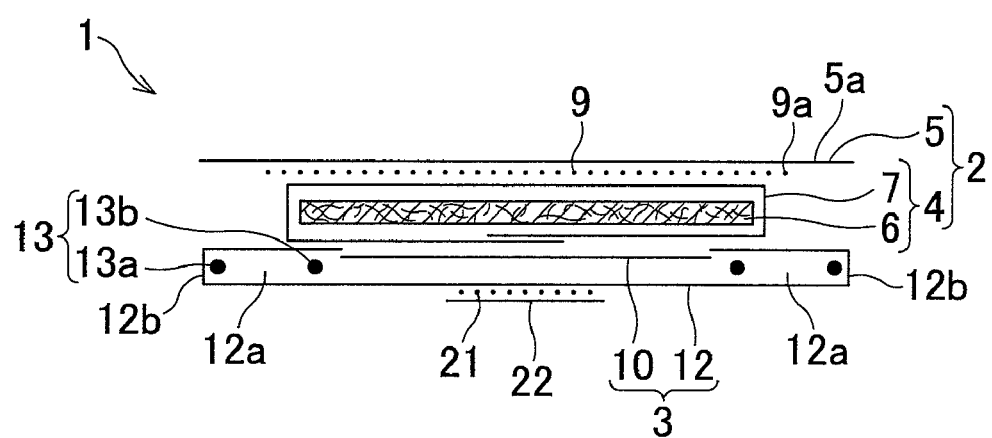
FIG. 2 is schematic sectional view taken along the line II-II in FIG. 1.

FIG. 1 is a perspective view of a breast milk absorbent pad as viewed from the outside and FIG. 2 is a schematic sectional view taken along the line II-II in FIG. 1. As will be apparent from FIG. 1, the breast milk absorbent pad includes a pad-chassis 1 externally shaped substantially in ellipsoid having its major axis extending in a longitudinal direction of the pad. The pad-chassis 1 comprises a body fluid absorbent layer 2 and a body fluid leak-barrier sheet 3. The body fluid absorbent layer 2 comprises a body fluid absorbent assembly 4 and a body fluid-previous inner sheet 5 covering an inner surface (corresponding to an upper surface as viewed in FIG. 2) of the body fluid absorbent assembly 4. The absorbent assembly 4 comprises a body fluid absorbent core 6 entirely wrapped with a body fluid-spreadable shape retaining sheet 7.

The core 6 is provided in the form of a panel primarily comprising fluff pulp with which super-absorbent polymer particles. This panel preferably has a basis weight in a range of 100 to 600 g/m$^2$. The shape retaining sheet 7 may be tissue paper or the like intermittently coated with hot melt adhesives (not shown) by means of which the shape retaining sheet 7 is fixed to the core 6. In this way, the shape retaining sheet 7 is kept to cover the core 6 so that the shape of the core 6 is reliably retained and materials of the core 6, particularly the polymer particles, are protected against falling off.

The inner sheet 5 facing the wearer's skin is formed preferably from a non-woven fabric made of thermoplastic synthetic fibers or a perforated film or more preferably by a non-woven fabric such as a spun bond or air-through non-woven fabric, in any case, having a basis weight in a range of 10 to 40 g/m$^2$. The inner sheet 5 is intermittently coated with hot melt adhesives 9 by means of which the inner sheet 5 is fixed to the absorbent assembly 4 so that the inner sheet 5 is maintained to cover the absorbent assembly 4. It is possible to exploit the inner sheet 5 as a multilayered structure comprising a non-woven fabric and a perforated film. Transversely opposite edges 5a (first portions) of the inner sheet 5 as well as transversely opposite edges 9a of the adhesives 9 coated region thereof extend outward beyond transversely opposite edges of the absorbent assembly 4.

The leak-barrier sheet 3 underlying the absorbent assembly 4 typically comprises a plastic film 10 preferably having a basis weight in a range of 10 to 40 g/m$^2$, a non-woven fabric 12 made of thermoplastic synthetic fibers preferably having a basis weight in a range of 10 to 40 g/m² and extending outward beyond outer peripheries of the film 10 and the absorbent assembly 4 so as to define the outer surface of the pad chassis 1 and to face the associated brassiere, and a laminated non-woven fabric preferably of spun bond/melt blown/spun bond (SMS) type. The film 10 and the non-woven fabric 12 are bonded together by means of hot melt adhesives (not shown) along transversely opposite edges of the film 10.

The outer surface of the pad-chassis 1 defined by the non-woven fabric is advantageously less slippery with respect to the associated wearing article such as a brassiere than the case in which the outer surface is defined by a plastic film and there is substantially unlikely that the breast milk absorbent pad might slip off from such wearing article. In addition, it is unnecessary to use any excessive amount of adhesive to prevent undesirable slippage of the pad and the area to be coated with adhesives as well as the amount of adhesives can be correspondingly reduced.

Transversely opposite edges of the non-woven fabric 12 are folded back inwardly of the pad-chassis 1 to form sleeves 12a. Lateral edges 12b (second portions) of the respective sleeves 12a extend outward beyond the lateral edges of the absorbent assembly 4 by substantially the same dimension as the lateral edges 5a of the inner sheet 5. In this regard, it is also possible to constitute the leak-barrier sheet from a plastic film and a thermoplastic non-woven fabric laminated on the outer surface of the plastic film so as to sandwich an elastically stretchable and contractible member 13 as will be describe later.

The pad chassis 1 includes end flaps 14 and side flaps 15 both defined by respective portions of the leak-barrier sheet 3 and the inner sheet 5 extending outward beyond the outer peripheral edge of the absorbent assembly 4 (See FIG. 1). More specifically, the side flaps 15 are respectively defined by the transversely opposite extension portions 5a of the inner sheet 5 and the transversely opposite extension portions 12b of the leak-barrier sheet 3. These extension portions 5a, 12b extend outward beyond the transversely opposite edges of the absorbent assembly 4 and are bonded together along transversely opposite edges 9a of the adhesives 9 coated regions respectively spaced inward from the outermost edges of the respective extension portions 5a, 12b. It should be noted that FIG. 2 illustrates the extension portions 5a, 12b before bonded along the transversely opposite edges 9a of the adhesives 9 coated regions.

The elastically stretchable and contractible member 13 comprises first and second elastically stretchable and contractible members 13a, 13b and elastically stretchable and contractible in a longitudinal direction Y. The first and second elastically stretchable and contractible members 13a, 13b are laid within the sleeves 12a of the leak-barrier sheet 3. Specifically, the first elastically stretchable and contractible members 13a extend along the transversely opposite edges of the respective sleeves 12a in the longitudinal direction Y while the second elastically stretchable and contractible members 13b underlie the transversely opposite edges of the absorbent assembly 4 spaced inward from the first elastically stretchable and contractible members 13a in a parallel relationship and extend along the edges of the absorbent assembly 4 in the longitudinal direction Y. These elastically stretchable and contractible members are respectively bonded, while they are stretched in the longitudinal direction Y, to the sleeves 12a by means of hot melt adhesives (not shown). A contractile force of the first elastically stretchable and contractible members 13a deforms the side flaps 15 so as to come in close contact with the wearer's skin while a contractile force of the second stretchable and contractible members 13b deforms the flat panel-like semirigid absorbent assembly 4 having a rigidity higher than those of the leak-barrier sheet 3 as well as the inner sheet 5 both having a high flexibility so that the absorbent assembly 4 inclusive of these sheets 3, 5, i.e., the pad-chassis 1 as a whole may be concavely curved with the inner sheet 5 inside, in other words, convexly curved with the leak-barrier sheet 3 outside.

These elastically stretchable and contractible members are fixed to the leak-barrier sheet along the transversely opposite edges thereof in this manner and therefore the transversely opposite edges 5a (first portions) of the inner sheet coming in close contact with the wearer's skin are free from being directly affected by a tensile stress of the elastically stretchable and contractible members. Consequentially, there is no anxiety that the transversely opposite edges 5a of the inner sheet might be formed with undesirable gathers which would cause the wearer to experience a feeling of discomfort and/or leave compression marks on the wearer's skin. Thus the transversely opposite edges 5a of the inner sheet are reliably held in close contact with the wearer's skin and thereby leak of breast milk can be effectively prevented.

The elastically stretchable and contractible member 13 is made of natural or synthetic rubber and preferably has a tensile force in a range of 115 to 500 mN.

A stretching ratio and a tensile force of the elastically stretchable and contractible member 13 are measured by a method described below.

A portion (referred to hereinafter as an effective length) of the elastically stretchable and contractible member 13 fixed in a stretched state having a length of 40 mm is cut away from the pad-chassis and adhesives clinging to the elastically stretchable and contractible member 13 is removed to obtain a specimen of the elastically stretchable and contractible member. The stretching ratio of the elastically stretchable and contractible member is obtained according to an equation of stretching ratio=40/W wherein W (mm) is a measured length of this specimen of the elastically stretchable and contractible member. The tensile force of the elastically stretchable and contractible member 13 is measured utilizing 5540 Series Single Column Tester System manufactured by INSTRON. Specifically, the specimen of the elastically stretchable and contractible member 13 is held by chucks spaced from each other by a distance of 30 mm, then stretched at a rate of 100 mm/min and the tensile force at the stretching ratio measured by said method is determined.

If the effective length is less than 40 mm, the length (W mm) of the elastically stretchable and contractible member 13 having such effective length cut away may be measured. In this case, the stretching ratio may be calculated according to the equation of stretching ratio=effective length/W and the tensile force may be measured by the method as has been described just above with the distance between the chucks set to the effective length minus 10 mm.

Figure 3:
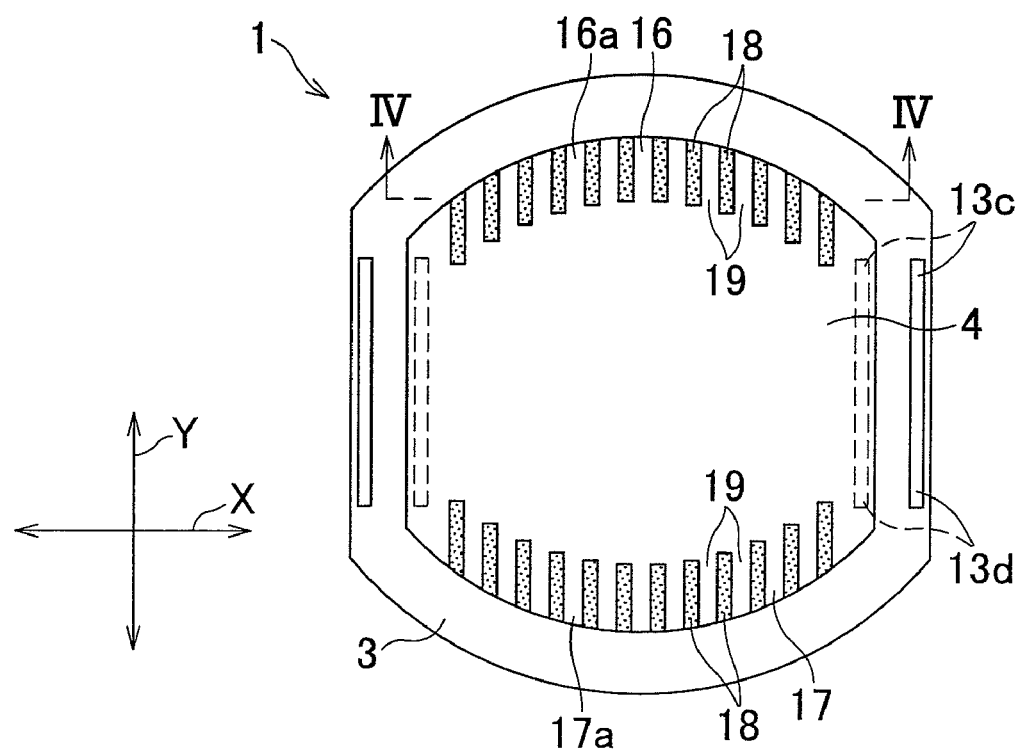
FIG. 3 is a plan view of the pad-chassis.
Figure 4:
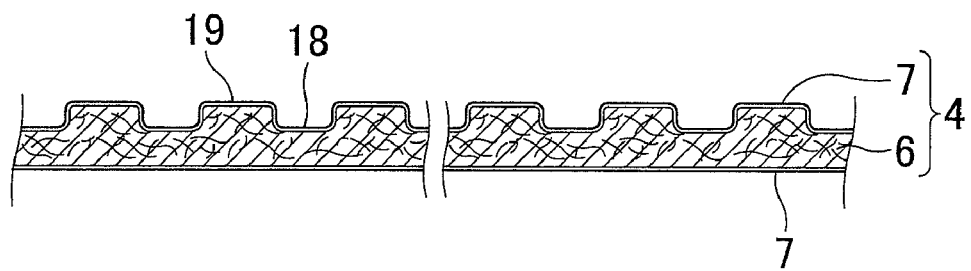
FIG. 4 is a sectional view taken along the line IV-IV in FIG. 3.

FIG. 3 is a plan view of the pad-chassis 1 having the inner sheet 5 removed and the sleeves 12a not shown and FIG. 4 is a sectional view taken along the line IV-IV in FIG. 3. The absorbent assembly 4 is provided along upper and lower ends thereof with embossed high stiffness regions 16, 17, respectively. The embossed regions 16, 17 have a higher stiffness in comparison to the remaining region. The high stiffness regions 16, 17 respectively comprise a plurality of embossed lines (i.e., compressed grooves) 18 and ridges 19 defined between each pair of the adjacent compressed grooves 18 both extending in the longitudinal direction Y so as to define together a surface repetitively patterned indented in the transverse direction X as will be apparent from FIG. 4. The absorbent assembly 4 is shaped substantially in ellipsoid and has the high stiffness regions 16, 17 describing circular arcs which are convex upward and downward, respectively. The leak-barrier sheet 3 and the inner sheet 5 (not shown) are also shaped substantially in ellipsoid so that the pad-chassis 1 is also shaped substantially in ellipsoid in its flat panel-like state free from a bowing effect of the elastically stretchable and contractible member 13. In the high stiffness regions 16, 17, the ridges 19 also are more or less compressed as the compressed grooves 18 are formed and consequentially these high stiffness regions 16, 17 as a whole have a thickness smaller than in the remaining region.

Specifically, the pad-chassis 1 has a thickness in a range of 3.0 mm to 3.8 mm in the embossed regions and a thickness in a range of 4.0 mm to 4.8 mm in the remaining region. The pad-chassis 1 constructed in the manner as has been described above can be smoothly inserted between the associated brassiere and the wearer's skin without a trouble that the upper end and/or the lower end of the pad-chassis 1 might be folded back.

At least the outermost ends 16a, 17a of the high stiffness regions 16, 17 as viewed in the longitudinal direction Y preferably extend outward beyond respective ends 13c, 13d of the elastically stretchable and contractible member 13. This is for the reason that the contractile force of the elastically stretchable and contractible member 13 will not directly act upon the respective outermost ends 13c, 13d extending outward beyond the respective ends 13c, 13d and therefore the upper and lower ends of the pad-chassis 1 can be further reliably prevented from being folded back. Although not shown, it is possible to emboss the absorbent assembly 4 together with the inner sheet 5 with which the absorbent assembly 4 is covered.

Figure 5:
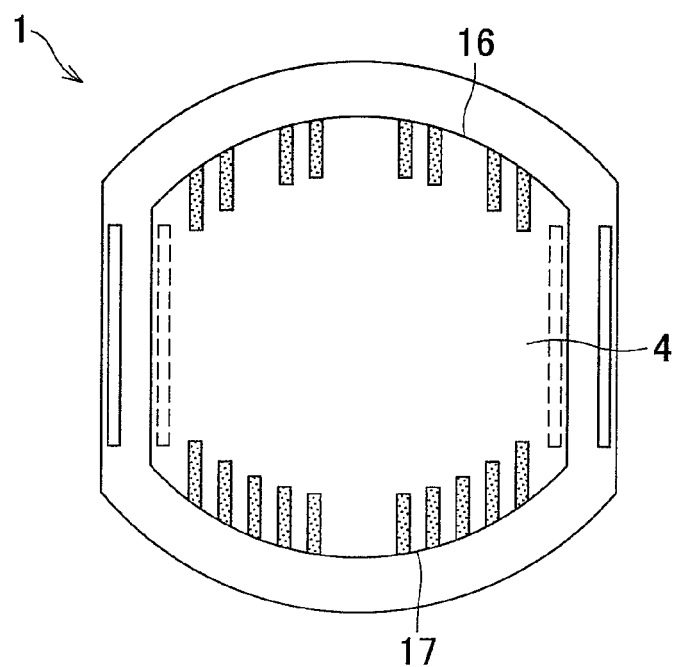
FIG. 5 is a plan view similar to FIG. 3, illustrating another emboss pattern.
Figure 6:
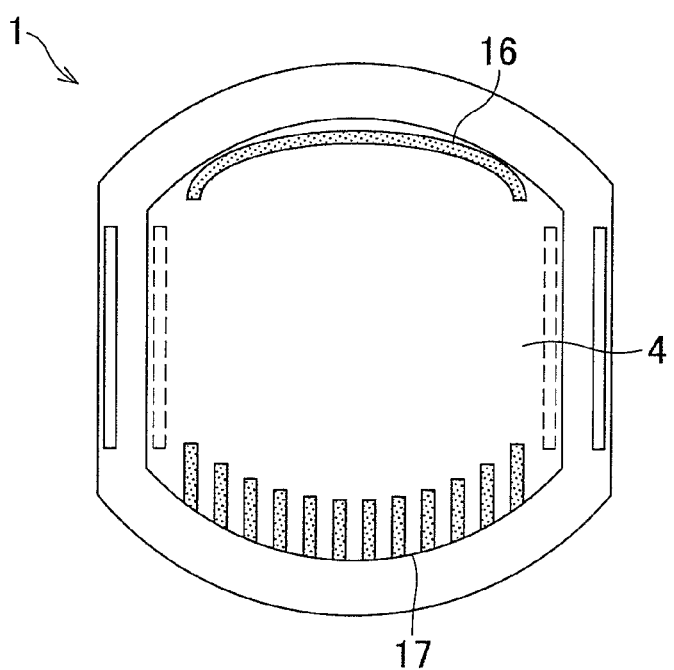
FIG. 6 is a plan view similar to FIG. 3, illustrating still another emboss pattern.

FIG. 5 is a plan view similar to FIG. 3, illustrating another embossing pattern. In this embossing pattern, the upper embossed region comprises a plurality of emboss lines extending in the longitudinal direction Y and these emboss lines comprise, in turn, a plurality of pairs of emboss lines spaced apart one from another. The lower embossed region is divided in tow sub-regions spaced from each other at the middle of the lower embossed region as viewed in the transverse direction X wherein each of the sub-regions comprises a plurality of emboss lines extending in the longitudinal direction Y.

FIG. 3 is a plan view similar to FIG. 3, illustrating still another embossing pattern. In this embossing pattern, the upper embossed region comprises a single emboss line extends in the transverse direction X, describing a circular arc which is convex upward while the lower embossed region comprises a plurality of emboss lines spaced apart one from another in the transverse direction and extending in the longitudinal direction Y in the same manner as in the embodiment shown by FIG. 3.

As has already been described, the embossing pattern is not limited to the embodiments as illustrated but may be optionally varied or modified, if desired.

Figure 7:
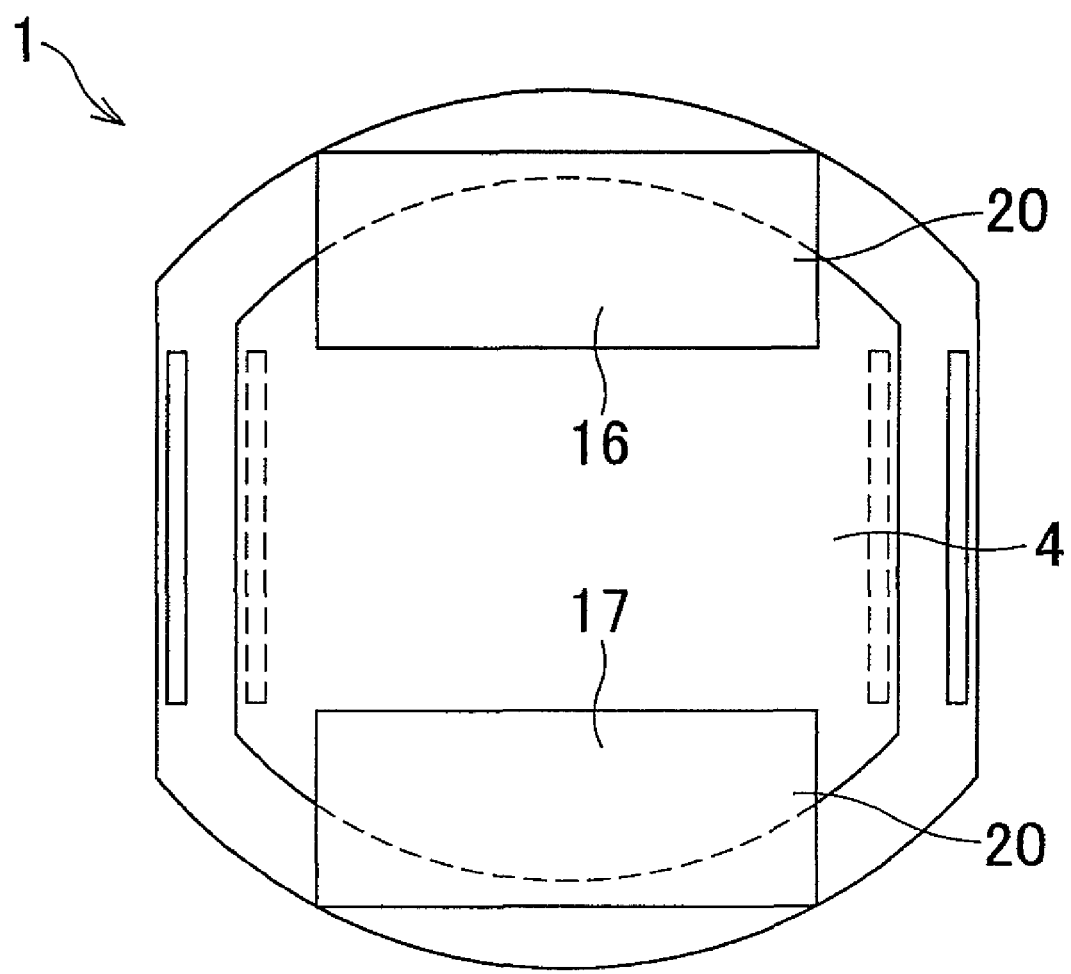
FIG. 7 is a plan view of an alternative embodiment in which a reinforcing layer is affixed to the outer surface of the absorbent assembly.

FIG. 7 is a plan view similar to FIG. 3, illustrating a manner in which a reinforcing layer 20 comprising a separately provided high basis weight non-woven fabric or an embossed non-woven fabric has been attached to each of the upper and lower ends of the absorbent assembly 4 instead of embossing the absorbent assembly 4. The reinforcing layer 20 is not limited to the above-mentioned non-woven fabric but may be formed from a layer of urethane foam or silicon or even by a layer of hot melt adhesive coated on the absorbent assembly 4.

The high stiffness regions 16, 17 have a flexural stiffness preferably in a range of 0.5 to 2.0 N·cm, more preferably in a range of 0.8 to 1.5 N·cm. The flexural stiffness of the embossed regions (i.e., high stiffness regions) is preferably in a range of 0.8 N·cm to 1.5 N·cm. So far as the flexural stiffness of the embossed regions is in such a range, there is no anxiety that the high stiffness regions as well as the upper and lower ends extending in the vicinity of these regions might be folded inward. If the flexural stiffness of the embossed regions is 0.8 N·cm or less, there is a possibility that the high stiffness regions as well as the upper and lower ends extending in the vicinity of these regions might be folded inward and if the flexural stiffness of the embossed regions is 1.5 N·cm or more, the excessively high stiffness may cause the wearer's skin to experience a feeling of discomfort.

While not illustrated, it is preferred to interpose a compression reversing elastic layer comprising a hydrophilic and/or hydrophobic fiber between the absorbent assembly 4 and the inner sheet 5 in order to alleviate the stiffness of the pad-chassis 1 containing the absorbent assembly 4 and to give the wearer a soft feeling to wear the breast milk absorbent pad.

Referring again to FIG. 1, the leak-barrier sheet 3 is coated on the outer surface thereof with a pressure-sensitive adhesive layer 21 by means of which the breast milk absorbent pad is affixed to the associated wearing article such as the brassiere and this pressure-sensitive adhesive layer 21 is covered with a separator 22.

The present invention may be exploited to produce the breast milk absorbent pad curved inward as a whole in conformity to a shape of breast so as to be smoothly put on with a good fitness without an anxiety that the high stiffness regions and the upper and lower ends lying adjacent these high stiffness regions might be unintentionally folded inward during putting on as well as during taking off of the pad.

The entire discloses of Japanese Patent application No. 2006-160341 filed on Jun. 8, 2006 including specification, drawings and abstract are herein incorporated by reference in its entirety.

What is claimed is:

1. A breast milk absorbent pad having a longitudinal direction and a transverse direction and comprising:
    a pad-chassis having a first surface facing a wearer's skin and a second surface facing away from the wearer's skin;
    said pad-chassis being composed of a body fluid absorbent layer inclusive of a body fluid absorbent assembly and a body fluid leak-barrier sheet defining said second surface, and a pair of elastically stretchable and contractible members extending along transversely opposite sides of said pad-chassis in said longitudinal direction in order to deform said first surface in a concave shape; and
    said body fluid absorbent assembly being provided with a high stiffness region having stiffness higher than in a region other than said high stiffness region, said high stiffness region being located exclusively so as to extend inward from a peripheral edge of the body fluid absorbent assembly at least one of upper and lower end portions as viewed in said longitudinal direction, without extending across a central portion of the body fluid absorbent assembly.

2. The breast milk absorbent pad as defined by claim 1, wherein at least an outer end of said high stiffness region as viewed in said longitudinal direction extends outward in said longitudinal direction beyond the associated end of said elastically stretchable and contractible member as viewed in said longitudinal direction.

3. The breast milk absorbent pad as defined by claim 1, wherein said body fluid absorbent layer comprises said body fluid absorbent assembly composed of a body fluid absorbent core wrapped with a body fluid-spreadable sheet and a body fluid pervious inner sheet facing the wearer's skin so as to cover said first surface of said body fluid absorbent assembly and said body fluid leak-barrier sheet comprises a body fluid impervious sheet.

4. The breast milk absorbent pad as defined by claim 1, wherein said high stiffness region is formed by embossing.

5. The breast milk absorbent pad as defined by claim 4, wherein said embossed high stiffness region is defined by a plurality of emboss lines spaced apart one from another by a given dimension in said transverse direction and extending in said longitudinal direction.

6. The breast milk absorbent pad as defined by claim 4, wherein said embossed high stiffness region is defined by at least one emboss line continuously extending in said transverse direction.

7. The breast milk absorbent pad as defined by claim 1, wherein said high stiffness region is provided on each of said upper and lower ends of said body fluid absorbent assembly.

8. The breast milk absorbent pad as defined by claim 1, wherein said high stiffness region has a thickness smaller than in a remaining region except said high stiffness region.

9. The breast milk absorbent pad as defined by claim 1, wherein said high stiffness region is formed from fixing a separately provided reinforcing layer to said body fluid absorbent assembly.

10. The breast milk absorbent pad as defined by claim 1, wherein said pad-chassis has side flaps extending outward from transversely opposite edges of said body fluid absorbent assembly in said transverse direction, said elastically stretchable and contractible member comprising first and second pairs of elastically stretchable and contractible members spaced apart from each other in said transverse direction, the elastically stretchable and contractible members constituting said first pair are attached to said side flaps along the respective outer edges thereof while the elastically stretchable and contractible members constituting said second pair are attached to said side flaps along the respective outer edges of said body fluid absorbent assembly.

11. The breast milk absorbent pad as defined by claim 10, wherein said body fluid absorbent layer comprises said body fluid absorbent assembly composed of a body fluid absorbent core wrapped with a body fluid-spreadable sheet and a body fluid pervious inner sheet facing the wearer's skin so as to cover said first surface of said body fluid absorbent assembly and said side flaps comprise first portions defined by said inner sheet and second portions placed upon said first portions and defined by said leak-barrier sheet and wherein said first pair of elastically stretchable and contractible members are attached to said second portions along the outer edges thereof while said second pair of elastically stretchable and contractible members are attached to said second portions along the inner edges thereof.

12. The breast milk absorbent pad as defined by claim 1, wherein elastically stretchable and contractible members are fixed within sleeves respectively formed by folding back transversely opposite edges of said leak-barrier sheet.

13. The breast milk absorbent pad as defined by claim 1, wherein said body fluid absorbent layer comprises said body fluid absorbent assembly composed of a body fluid absorbent core wrapped with a body fluid-spreadable sheet and a body fluid pervious inner sheet facing the wearer's skin so as to cover said first surface of said body fluid absorbent assembly and said inner sheet comprises a body fluid pervious fibrous non-woven fabric and at least the transversely opposite edges of said leak-barrier sheet comprise a hydrophobic fibrous non-woven fabric.

14. The breast milk absorbent pad as defined by claim 1, wherein said pad-chassis has end flaps extending outward from upper and lower ends of said body fluid absorbent assembly in said longitudinal direction.

15. The breast milk absorbent pad as defined by claim 1, wherein said pad-chassis has a substantially elliptical outer shape.

\* \* \* \* \*